(12) United States Patent
Cichon et al.

(10) Patent No.: US 11,471,124 B2
(45) Date of Patent: Oct. 18, 2022

(54) MEDICAL IMAGING TABLE, TABLE SUPPORT ASSEMBLY, PROBE SUPPORT ASSEMBLY, SYSTEM, AND METHOD OF USE

(71) Applicant: REGENERON PHARMACEUTICALS, INC., Tarrytown, NY (US)

(72) Inventors: Sam Cichon, Tarrytown, NY (US); Michael E. Dunn, Tarrytown, NY (US)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 825 days.

(21) Appl. No.: 16/461,472

(22) PCT Filed: Nov. 15, 2017

(86) PCT No.: PCT/US2017/061723
§ 371 (c)(1),
(2) Date: May 16, 2019

(87) PCT Pub. No.: WO2018/093845
PCT Pub. Date: May 24, 2018

(65) Prior Publication Data
US 2019/0328500 A1 Oct. 31, 2019

Related U.S. Application Data

(60) Provisional application No. 62/538,872, filed on Jul. 31, 2017, provisional application No. 62/422,863, filed on Nov. 16, 2016.

(51) Int. Cl.
*A61B 8/00* (2006.01)

(52) U.S. Cl.
CPC .............. *A61B 8/40* (2013.01); *A61B 8/4218* (2013.01)

(58) Field of Classification Search
None
See application file for complete search history.

(56) References Cited

U.S. PATENT DOCUMENTS 4,431,007 A 2/1984 Amazeen et al.
4,481,657 A * 11/1984 Larsson ............... A61B 6/0464
378/91

(Continued)

OTHER PUBLICATIONS

International Search Report dated Aug. 1, 2018 issued in PCT/US2017/061723.

*Primary Examiner* — Luther Behringer
(74) *Attorney, Agent, or Firm* — Scully, Scott, Murphy & Presser, P.C.; Brandon T. Schurter

(57) ABSTRACT

A system including: a table assembly for supporting a subject in one or more examination positions; a table support assembly for supporting the table assembly, wherein the table support assembly includes: one or more moving mechanisms controlled to move the table assembly relative to a reference point along one or more axes, and to rotate the table assembly around the one or more axes; and a probe support assembly comprising: a grip for holding a probe; and an arrangement of a plurality of arms and joints controlled to movably support the probe that is held by the grip, wherein the probe support assembly is removably arranged at a predetermined position and orientation relative to the table support assembly to permit movement of the table support assembly and the probe support assembly for reproduction of a position and orientation of the probe relative to the subject supported by the table assembly.

16 Claims, 9 Drawing Sheets

(56) References Cited

U.S. PATENT DOCUMENTS

| | | |
|---|---|---|
| 2005/0215878 A1 | 9/2005 | Zan |
| 2013/0025055 A1 | 1/2013 | Saracen et al. |
| 2015/0011875 A1 | 1/2015 | Noordhoek et al. |
| 2015/0265243 A1* | 9/2015 | Kelly .................. A61B 8/4218 600/443 |
| 2017/0000675 A1* | 1/2017 | Hight .................. A61B 6/0407 |

* cited by examiner

MEDICAL IMAGING TABLE, TABLE SUPPORT ASSEMBLY, PROBE SUPPORT ASSEMBLY, SYSTEM, AND METHOD OF USE

CROSS REFERENCE TO RELATED APPLICATION

This application claims the benefit of priority from U.S. Provisional Application No. 62/422,863, filed Nov. 16, 2016 and U.S. Provisional Application No. 62/538,872, filed Jul. 31, 2017, the entire contents of which are incorporated herein by reference.

BACKGROUND

The present invention relates to a system and a method of positioning a subject S and a probe P of an imaging equipment during acquisition of a first image at a first time and a second image at a second time after the first time. The first image can be a pre-treatment image acquired prior to performance of a treatment on the subject S, and the second image can be a post-treatment image acquired after the performance of the treatment on the subject S.

The subject S can be a human subject or a primate such as an African-green monkey.

The imaging equipment can be an ultrasound imaging device. The probe P can be a handheld probe that is conventionally held and operated by a user. The probe P can include one or more ultrasound transducers configured to convert electrical signals into ultrasound that is emitted towards the subject S, receive ultrasound returned from the subject S and convert the received ultrasound into electrical signal. The electrical signal converted from the received ultrasound can be processed to generate an image of the subject S.

SUMMARY

Figure 1:
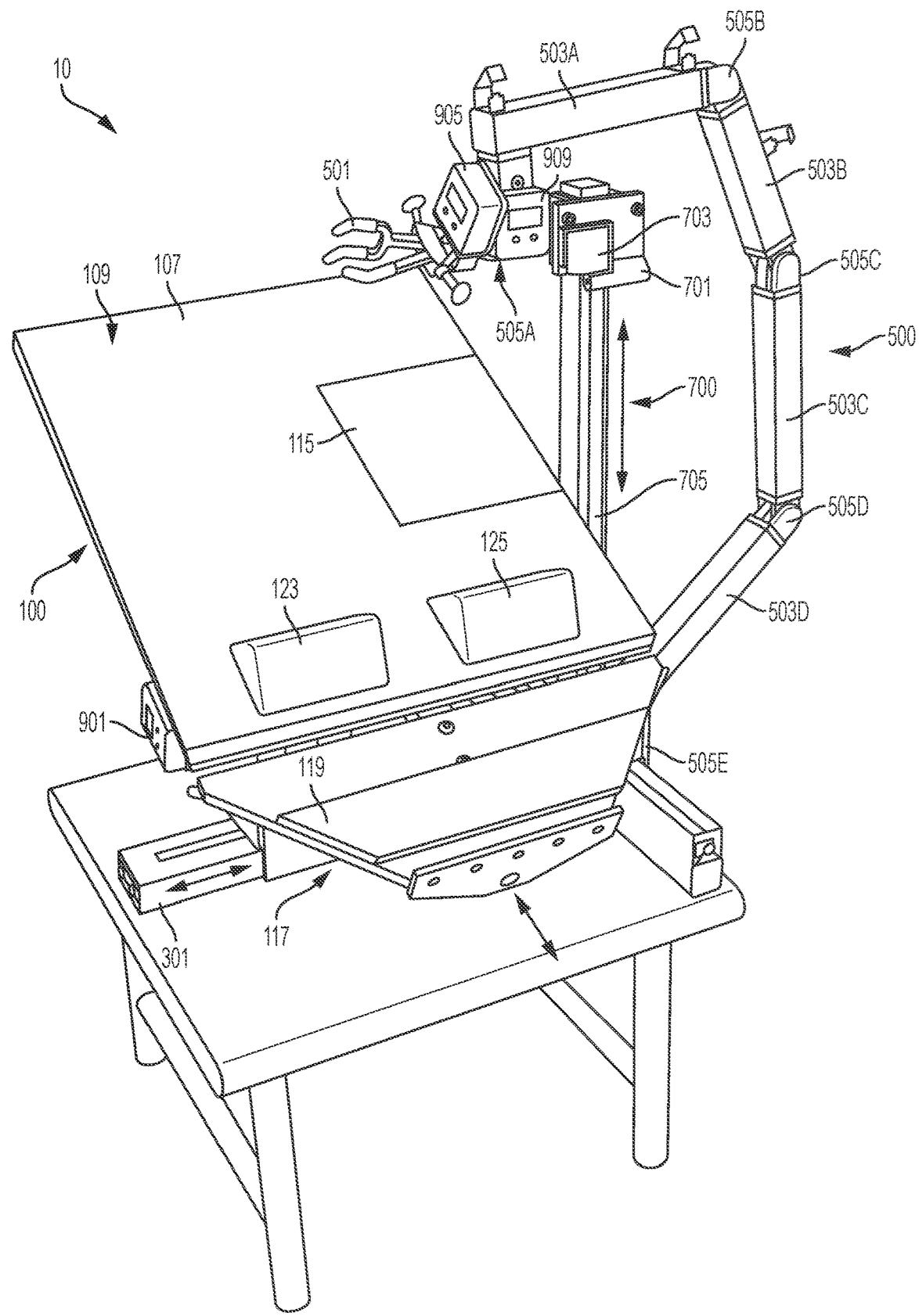
FIG. 1 shows a system according to one aspect of the invention, the system including a table, a table support assembly, a probe support assembly and an actuator assembly from a first point of view.

The present invention provides a system comprises: a table assembly configured to support a subject in one or more examination positions; a table support assembly configured to support the table assembly, wherein the table support assembly comprises: one or more moving mechanisms configured to be controlled to move the table assembly relative to a reference point along one or more axes, and to rotate the table assembly around the one or more axes; and a probe support assembly comprising: a grip configured to hold a probe of an imaging device; and an arrangement of a plurality of arms and joints configured to movably support the probe that is held by the grip, wherein the plurality of arms and joins provide multiple degrees of freedom, wherein the probe support assembly is removably arranged at a predetermined position and orientation relative to the table support assembly to permit movement of the one or more moving mechanisms of the table support assembly and the plurality of arms and joints of the probe support assembly for reproduction of a position and orientation of the probe relative to the subject supported by the table assembly.

The present invention further provides a method comprising: repeating a process of: positioning a subject to be supported by a table assembly in an examination position; controlling one or more moving mechanisms of a table support assembly supporting the table assembly to move the table assembly relative to a reference point along one or more axes, and to rotate the table assembly around the one or more axes; operating a grip of a probe support assembly to hold a probe of an imaging device; and controlling an arrangement of a plurality of arms and joints of the probe support assembly, wherein the plurality of arms and joints provide multiple degrees of freedom, to movably support the probe that is held by the grip, wherein the process is repeated such that the probe support assembly is removably arranged at a predetermined position and orientation relative to the table support assembly to permit movement of the one or more moving mechanisms of the table support assembly and the plurality of arms and joints of the probe support assembly for reproduction of a position and orientation of the probe relative to the subject supported by the table assembly.

DETAILED DESCRIPTION

It is to be understood that this invention is not limited to the particular apparatus, assembly, system, and method of use described, as such apparatus, assembly, system, and method of use may vary. It is also to be understood that the terminology used herein is for the purpose of describing particular embodiments only, and is not intended to be limiting.

As used in this specification, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice of the present invention, particular methods and materials are now described.

A system 10 according to one aspect of the invention is described below with reference to FIGS. 1-5 of the drawings. The system 10 can include a table 100, a table support assembly 300, a probe support assembly 500, an alignment assembly 700, a sensor assembly 900, an actuator assembly 1100 and a controller 1300.

The table 100 is described below with reference to FIGS. 1-5 of the drawings.

The table 100 can include a first table frame 101. The first table frame 101 can include a substantially planar structure having a first table frame upper surface 103 and a first table frame lower surface opposing the first table frame upper surface 103. The dimensions of the planar structure of the first table frame 101 can be selected based on the dimensions of a subject S to allow the subject S to be supported in a supine position or a prone position where a largest surface area of the subject S is in contact with the table 100. As an example, a length of the first table frame 101 can be selected to be equal to or longer than a maximum length of the subject S along a superior-inferior axis direction from a head of the subject S to a hip of the subject S. As an example, a width of the first table frame 101 can be selected to be equal to or longer than a maximum length of the subject S along a medial-lateral axis from a left shoulder to a right shoulder of the subject S.

The table 100 can include a first cushion 107 that is supported by the first table frame upper surface 103. The first cushion 107 can include a first cushion upper surface 109 and a first cushion lower surface 111 opposite to the first cushion upper surface 109. The first cushion lower surface 111 can contact the first table frame upper surface 103 such that the first cushion 107 is supported by the first table frame upper surface 103. The first cushion upper surface 109 can contact the subject S to support the subject S in one or more examination positions. The first cushion 107 can include a deformable material that is selected to improve the comfort of the subject S that is supported by the first cushion 107. Further, the deformable material can be selected to dampen or minimize movement of the subject S as the subject S is supported by the first cushion 107.

Figure 2:
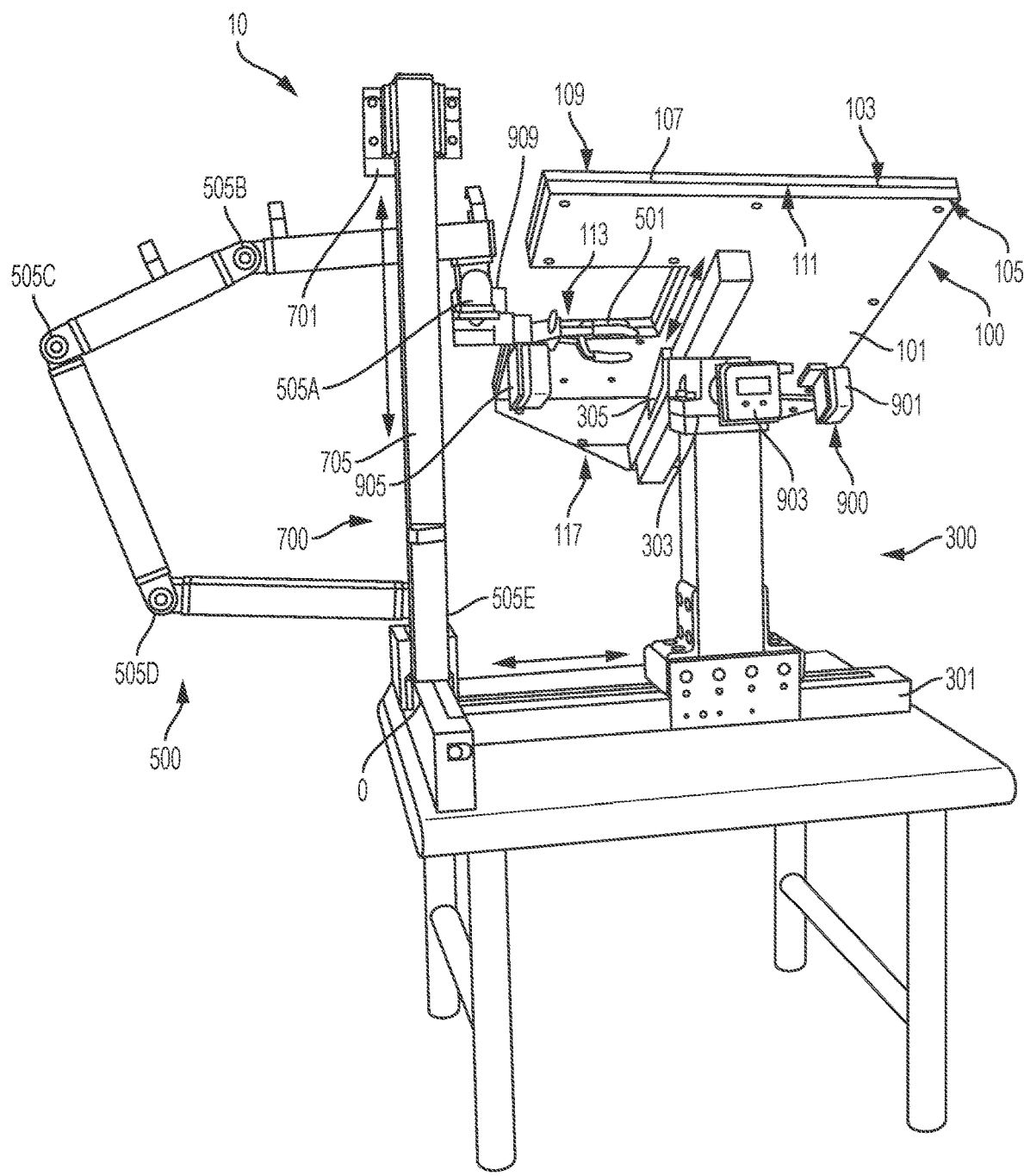
FIG. 2 shows the system from a second point of view.
Figure 4:
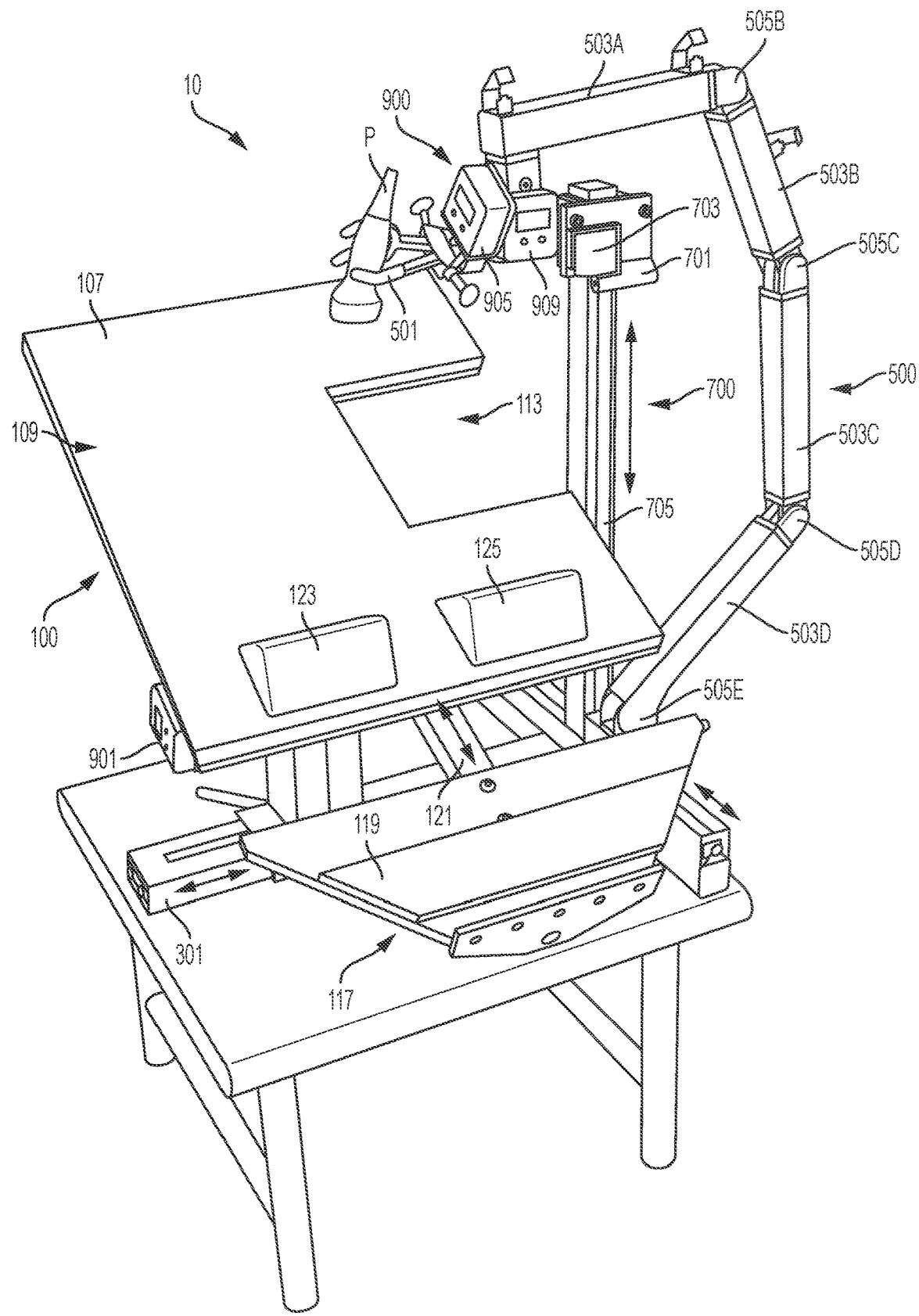
FIG. 4 shows the system from the first point of view, wherein a shiftable surface of the table is positioned in a different position than in FIG. 1.

The first cushion 107 and the first table frame 101 can be configured to define an access space 113. As an example, the access space 113 can be carved out of a lateral side of the first table frame 101 and the first cushion 107 as shown in FIGS. 2 and 4. The access space 113 allows for a probe P to approach the subject S supported by the table 100 from a side of the first table frame lower surface 105. In a case where the subject 100 is supported by the table 100 in a left lateral recumbant position, the access space 113 allows for the probe P to approach the subject S from the side of the first table frame lower surface 105 to be closer to a left side of a thoracic cage of the subject S. The position of the access space 113 is not limited to that shown in FIGS. 2 and 4. The access space 113 can also be positioned in an interior position of the first table frame 101 and the first cushion 107.

The table 100 can include a second table frame 117 arranged on an inferior side of the first table frame 101 closest to an inferior portion (e.g., the hip) of the subject S as the subject S is supported by the first table frame 101. The second table frame 117 can include a substantially planar structure having dimensions selected based on the dimensions of a portion of the subject S that is not supported by the first table frame 101. As an example, a length of the second table frame 117 can be selected to be equal to or longer than a maximum length of the subject S along the superior-inferior axis direction from the knees of the subject S to the feet of the subject S.

The table 100 can include a second cushion 119 that is supported by the second table frame 117. The second cushion 119 can support the portion of the subject S that is not supported by the first table frame 101.

The table 100 can include an adjustable connector 121, as shown in FIG. 4, configured to connect the first table frame 101 and the second table frame 117. As an example, the adjustable connector 121 can include a telescoping structure or a guide structure that allows for adjusting a distance between the first table frame 101 and the second table frame 117 in a length direction of the first table frame 101 to accommodate a height dimension of the subject S. As an example, the adjustable connector 121 can include one or more rotatable joint structures that allow the second table frame 117 to rotate relative to the first table frame 101 along an axis substantially parallel to the inferior side of the first table frame 101 to allow for the subject S to be supported in one or more positions. For example, the one or more rotatable joint structures of the adjustable connector 121 can be rotated to rotate the second table frame 117 relative to the first table frame 101 such that the knees of the subject S can be bent while the subject S is supported by the first table frame 101 and the second table frame 117.

The table 100 can include a shiftable surface 115 configured to shift relative to the first table frame 101 and the first cushion 107 between a first position as shown in FIG. 1 and a second position as shown in FIG. 2. In the first position, the shiftable surface 115 is arranged in the access space 113 to support the subject S. In the second position, the shiftable surface 115 is arranged away from the access space 113 to permit the probe P to access the subject S from the side of the first table frame lower surface 105. FIG. 2 shows an exemplary configuration where the shiftable surface 115 is separated from the first table frame 101 and the first cushion 107. The shiftable surface 115 is not limited to such a configuration. In another exemplary configuration, the shiftable surface 115 can be connected to the first table frame 101 by a rotatable joint structure such as a hinge. The hinge can be manipulated to swing the shiftable surface 115 between the first position to arrange the shiftable surface 115 in the access space 113, and the second position to arrange the shiftable surface 115 away from the access space 113.

Figure 5:
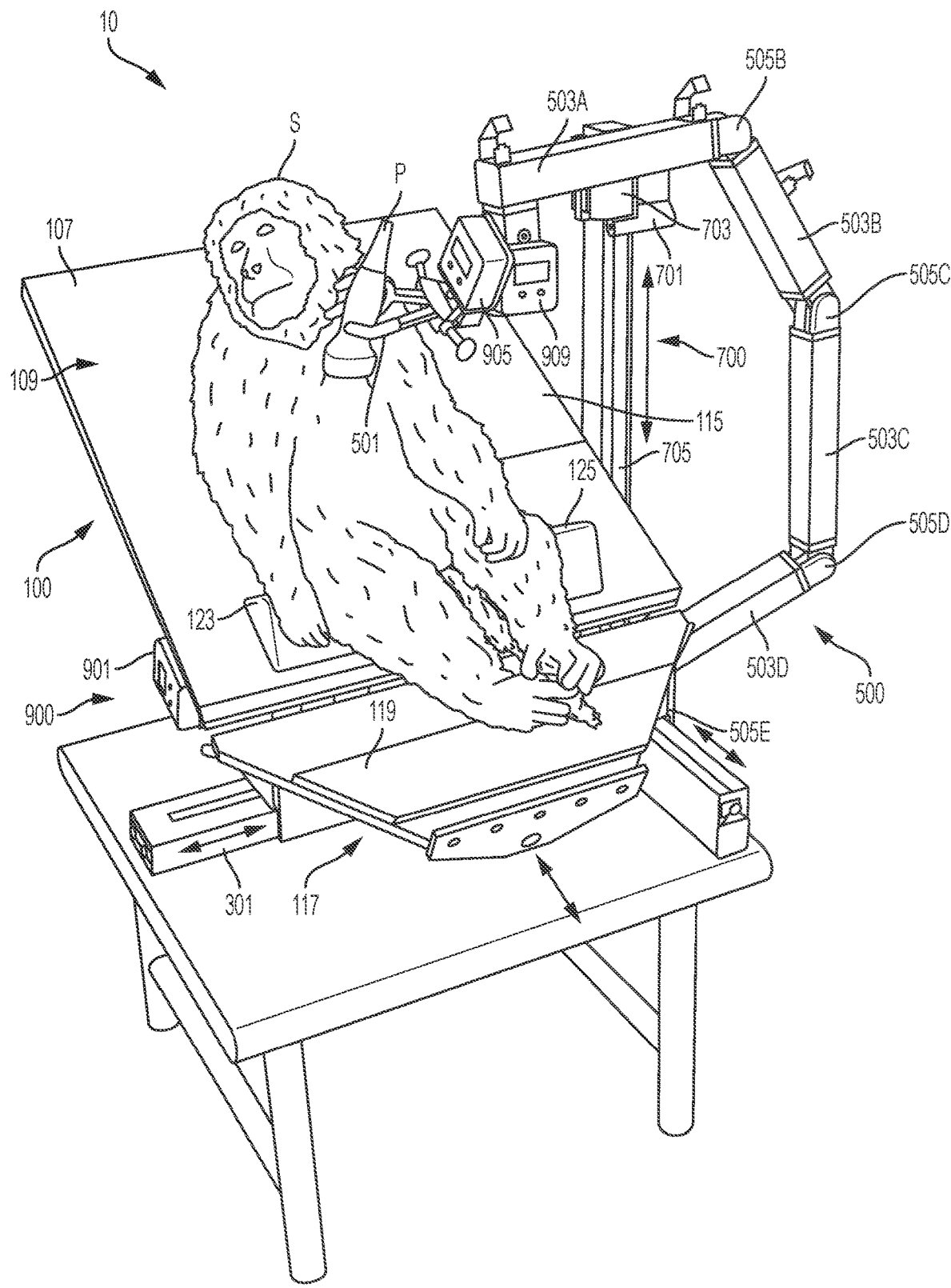
FIG. 5 shows the system from the first point of view, wherein the system is in use to image a subject.

The table 100 can include one or more positioning surfaces configured to position the subject S in a desired position and minimize movement by the subject S after being positioned in the desired position. The one or more positioning surfaces can be attached to the first cushion 107. Alternatively, the one or more positioning surfaces can be detachably attached, for example, by mechanical based fastening structures, to the first cushion 107. An example of the mechanical based fastening structures can include a hook and loop fastener. The one or more positioning surfaces can include a first positioning surface 123 and a second positioning surface 125 as shown in FIGS. 1, 4 and 5. The first positioning surface 123 and the second positioning surface 125 can be attached closer to the inferior side of the first table frame 101. The first positioning surface 123 and the second positioning surface 125 can be positioned to be spaced apart from each other along the medial-lateral axis of the first table frame 101. In a case where the subject S is a primate having an elongated tail, the subject S can be supported by the table 100 in a semi-Fowler position as shown in FIG. 5. The subject S is positioned to lie on the first cushion 107 in a supine position with the first table frame 101 being tilted by a table support assembly to be described below. In the semi-Fowler position the first positioning surface 123 and the second positioning surface 125 can support the buttocks of the subject S and prevent the subject S from sliding in a direction of gravity from the first table frame 101 that is tilted. Further, the elongated tail of the subject S can be accommodated in the space between the first positioning surface 123 and the second positioning surface 125.

The table 100 can include one or more restraining structures (not shown) configured to restrain or reduce the movement of the subject S while the subject S is supported by the table 100 in a desired position. An example of a restraining structure can include a strap configured to secure the subject S in the desired position. Another example of a restraining structure can include a tie configured to be threaded through perforations provided in the first table frame 101 and the second table frame 117 to secure the subject S in the desired position.

Figure 3:
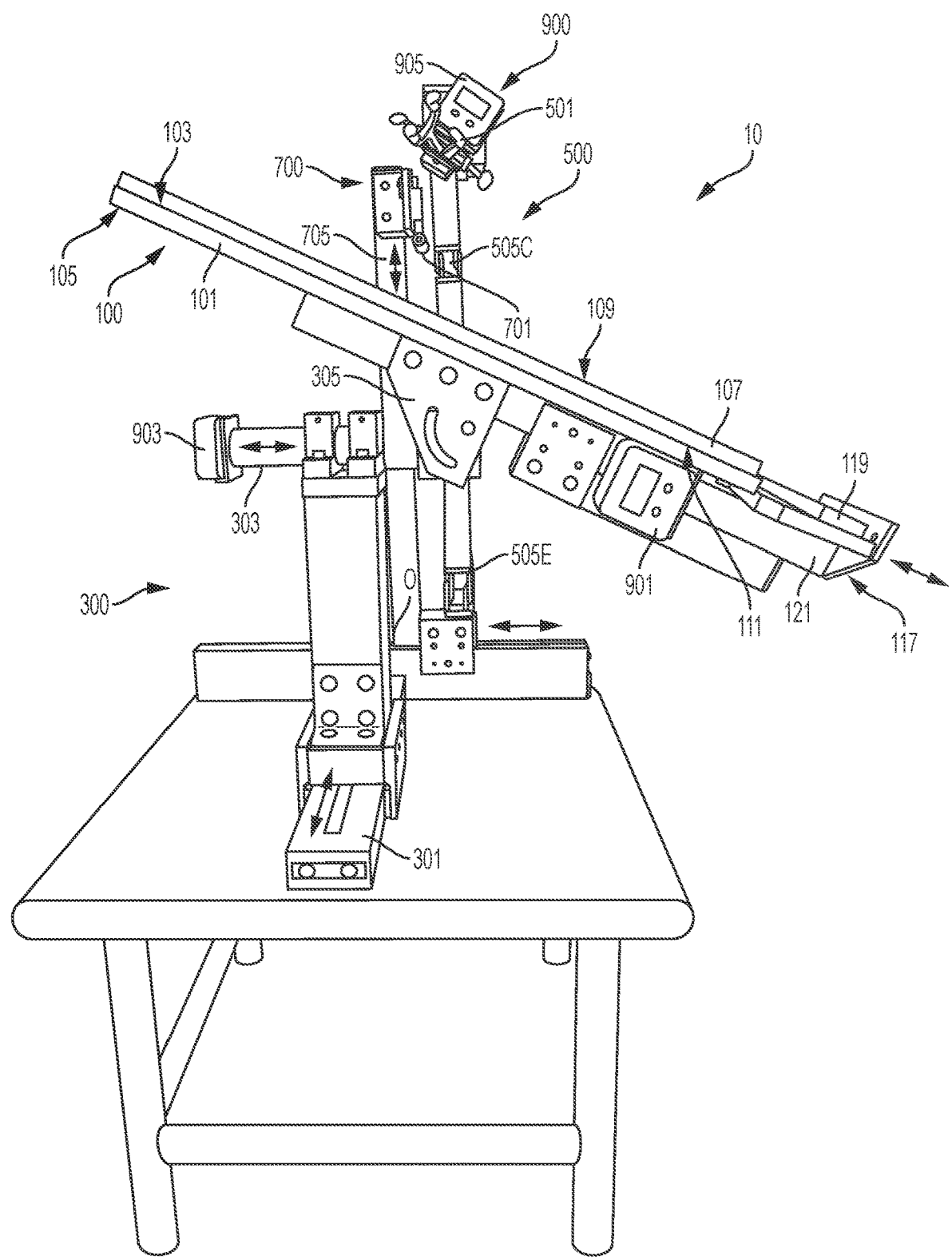
FIG. 3 shows the system from a third point of view.

The table support assembly 300 is described below with reference to FIGS. 2 and 3 of the drawings.

The table support assembly 300 can be configured to movably support the table 100. The table support assembly 300 can include one or more moving mechanisms configured to support and move the table 100 relative to an arbitrary origin O, as a reference point. The one or more moving mechanisms can include an X-axis guide mechanism 301 configured to guide the table 100 along an arbitrary X-axis relative to the arbitrary origin O. The one or more moving mechanisms can include an Y-axis guide mechanisms 303 configured to guide the table 100 along an arbitrary Y-axis relative to the arbitrary origin O. The one or more moving mechanisms can include a X-axis rotation mechanism 305 configured to rotate the table 100 about the X-axis.

As an example, each of the X-axis guide mechanism 301 and the Y-axis guide mechanism 303 are further configured to rotate about the X-axis and the Y-axis, respectively. As illustrated in FIG. 2, the Y-axis guide mechanism 303 can include a cylindrical bar that can be moved along the Y-axis to thereby move the table 100 attached to the Y-axis guide mechanism 303 along the Y-axis. Further, the cylindrical bar can be rotated about the Y-axis to change an inclination of the table 100 about the Y-axis.

The one or more moving mechanisms of table support assembly 300 are not limited to the X-axis guide mechanism 301, the Y-axis guide mechanism 303 and the X-axis rotation mechanism 305. The one or more moving mechanisms of table support assembly 300 can include additional moving mechanisms configured to guide the table 100 along one or more of the X-axis, the Y-axis and the Z-axis, and to rotate the table 100 about the X-axis, the Y-axis and the Z-axis.

The table support assembly 300 can include one or more lock mechanisms configured to releasably lock the one or more moving mechanisms to secure the table 100 to a desired position and orientation relative to the arbitrary origin O.

The table support assembly 300 can include one or more table support assembly-side markers. The table support assembly-side markers can be configured to indicate a position of the table 100 relative to the arbitrary origin O along the X, Y and Z-axes, and a degree of inclination of the table 100 about the X, Y and Z-axes. The table support assembly-side markers allow for manual recordation of the a position and an inclination of the table 100 at a first time, and for the position and the inclination of the table 100 to be reproduced at a second time through manipulation of the one or more moving mechanisms.

The probe support assembly 500 is described below with reference to FIGS. 1, 2, 4 and 5 of the drawings.

The probe support assembly 500 can include a grip 501 configured to hold the probe P. The probe, as illustrated in FIGS. 1, 2, 4 and 5 can include three movable fingers that can releasably grip the probe P.

The probe support assembly 500 can include an arrangement of one or more arms and joints configured to movably support the grip 501 holding the probe P to position the probe P at an arbitrary position and orientation relative to the arbitrary origin O. As an example, the arrangement of the one or more arms and joints can include arms 503A-D and joints 505A-E. The joint 505A can be configured to rotate the grip 501 about an axis parallel to the X-axis. The joint 505 A can be further configured to rotate the grip 501 about an axis parallel to the Y-axis. Further, the joint 505B can be configured to rotate the arm 503A about an axis parallel to the Y-axis. Further, the joint 505C can be configured to rotate the arm 503B about another axis parallel to the Y-axis. Further, the joint 505D can be configured to rotate the arm 503C about another axis parallel to the Y-axis. Further, the joint 505E can be configured to rotate the arm 503D about another axis parallel to the Y-axis. The joint 505E can be positioned at an arbitrary position along the Y-axis from the arbitrary origin O.

The one or more arms and joints of the probe support assembly 500 are not limited to the arms 503A-D and the joints 505A-E. The one or more arms and joints can include additional arms and joints to provide multiple degrees of freedom. As an example, addition joints can be provided to rotate the joint 505E about an axis parallel to the Z-axis.

The probe support assembly 500 can include one or more probe assembly-side markers. The one or more probe assembly-side markers can be configured to indicate a position of the probe P relative to the arbitrary origin O along the X, Y and Z-axes, and an orientation of the probe P about the X, Y and Z-axes. As an example, the probe assembly-side markers can indicate degrees of rotation about each of the joints 505A-E. The probe assembly-side markers allow for manual recordation of the position and the inclination of the probe P at the first time, and for the position and the inclination of the probe P to be reproduced at a second time through manipulation of the joints 505A-E.

The probe support assembly 500 can include one or more lock mechanisms configured to releasably lock one or more of the joints 505A-E to secure the probe B to a desired position and orientation relative to the arbitrary origin O.

The alignment assembly 700 is described below with reference to FIGS. 1-5 of the drawings.

The alignment assembly 700 can be configured to align one or more of the probe P, the subject S, the table 100, the table support assembly 300 and the probe support assembly 500 to each other.

The alignment assembly 700 can include a sight 701, a tape measure 703 and one or more guide mechanisms for guiding the sight 701 and the tape measure 703 along one or more axis.

The sight 701 can include a bore through which a user can optically align one or more of the probe P, the subject S, the table 100, the table support assembly 300 and the probe support assembly 500 to a known arbitrary position of the sight 701.

The sight 701 is not limited to a bore. The sight 701 can also include a laser that can be operated by the user to align one or more of the probe P, the subject S, the table 100, the table support assembly 300 and the probe support assembly 500 to the arbitrary position of the sight 701.

The tape measure 703 can be attached to the sight 701 at a known arbitrary position relative to the known arbitrary position of the sight 701. The tape measure 703 can be a retractable tape measure that can be employed by the user to measure and set a distance from the known arbitrary position of the sight 701 to one or more of the probe P, the subject S, the table support assembly 300 and the probe support assembly 500.

The one or more guide mechanisms for guiding the sight 701 and the tape measure 703 can include a Z-axis guide mechanism 705. As an example, the Z-axis guide mechanism 705 can extend from the arbitrary origin O in the Z-axis, wherein the sight 701 and the tape measure 703 can be moved along the Z-axis guide mechanism 705.

The sensor assembly 900 is described below with reference to FIGS. 1-5 of the drawings.

The sensor assembly 900 can include one or more table support assembly-side sensors. As an example, the one or more table support assembly-side sensors can include an X-axis table support assembly-side sensor 901 and an Y-axis table support assembly-side sensor 903. The X-axis table support assembly-side sensor 901 can be configured to sense and output an amount of rotation of the X-axis rotation mechanism 305 about the X-axis as a measure of an amount of rotation of the table 100 about the X-axis. The Y-axis table support assembly-side sensors 903 can be configured to sense and output an amount of rotation of the Y-axis guide mechanism 303 as a measure of an amount of rotation of the table 100 about the Y-axis.

The sensor assembly 900 can include one or more probe assembly-side sensors. As an example, the one or more probe assembly-side sensors can include an X-axis probe support assembly-side sensor 907 and an Y-axis probe support assembly-side sensor 909.

The X-axis probe support assembly-side sensor 903 can be configured to sense and output an amount of rotation of the joint 505 about an axis parallel to the X-axis as a measure of an amount of rotation of the probe P about the axis parallel to the X-axis. The Y-axis probe support assembly-side sensors 907 can be configured to sense and output an amount of rotation of the joint 505 about an axis parallel to the Y-axis as a measure of an amount of rotation of probe P about the Y-axis.

The sensor assembly 900 can include one or more sensors that can be configured to detect and output a position of the table 100 along one or more of the X-axis, Y-axis and Z-axis relative to the arbitrary origin O, and an inclination of the table 100 about one or more of the X-axis, Y-axis and Z-axis. Similarly, the sensor assembly 900 can include one or more sensors that can be configured to detect and output a position of the probe P along one or more of the X-axis, Y-axis and Z-axis relative to the arbitrary origin O, and an orientation of the probe P.

In the sensor assembly 900, an example of a sensor configured to sense an amount of rotation is a rotary ring encoder or the like positioned on a rotating or hinged joint.

Figure 6:
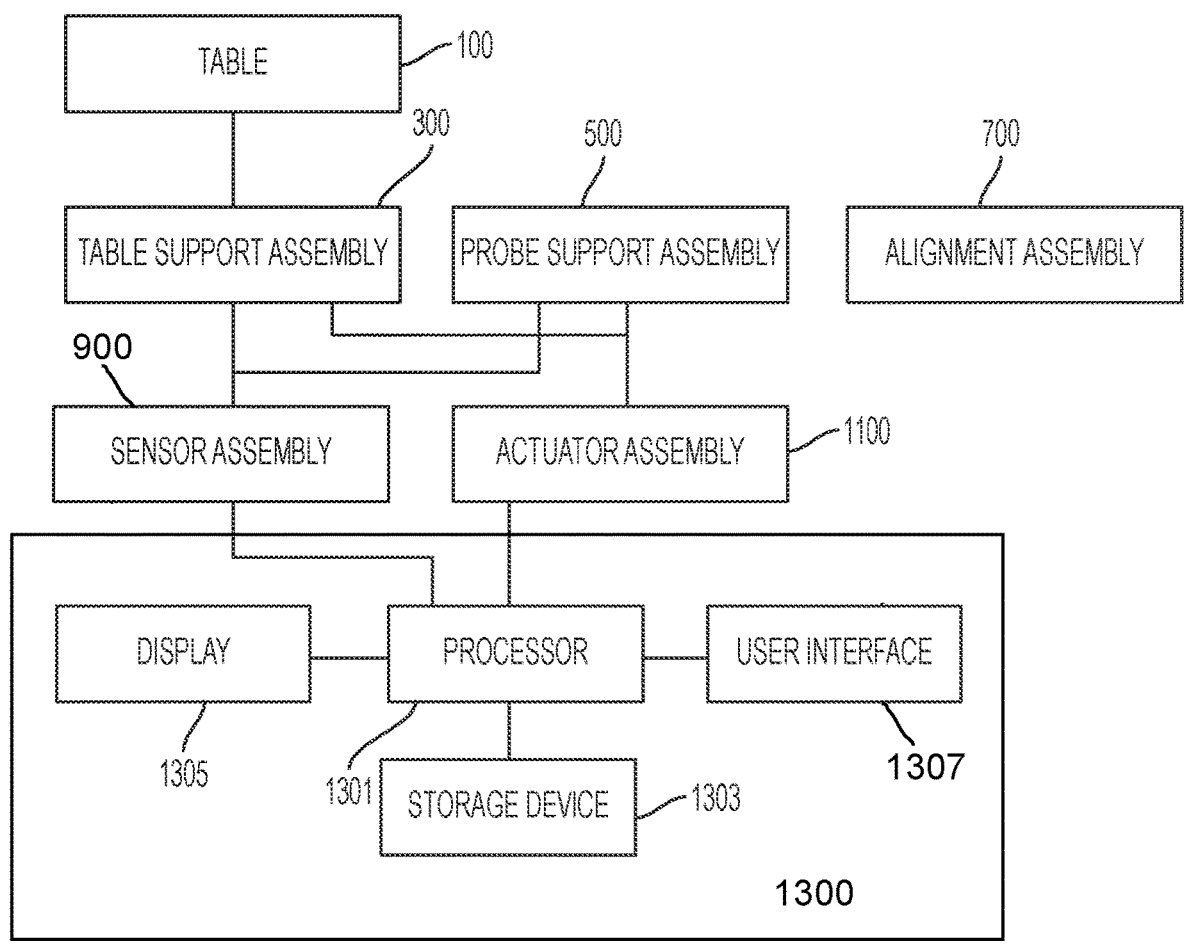
FIG. 6 shows a block diagram of the system, wherein the system includes an actuator assembly and a controller.

The actuator assembly 1100 is described below with reference to FIG. 6 of the drawings. The actuator assembly 1100 can include one or more actuators. The one or more actuators can be configured to be controlled by the controller 1300, to be described below, to move the X-axis guide mechanism 301, the Y-axis guide mechanism 303 and the X-axis rotation mechanism 305 of the table support assembly 300 to thereby move and/or rotate the table 100. Further, the one or more actuators can be configured to be controlled by the controller 1300 to move the joints 505A-E of the probe support assembly 500 to move and/or rotate the probe P gripped by the grip 501.

The controller 1300 is described below with reference to FIG. 6 of the drawings.

The controller 1300 can include one or more processors 1301 comprising hardware (such as a computer or processing circuits), one or more storage devices 1303 (such as one or more memories), a display 1305 and an user interface device 1307.

The one or more storage devices 1303 can be configured to store instructions that, when executed by the one or more processors 1301, cause the one or more processors 1301 to receive table support assembly-side data output by and indicative of the positions of the one or more table support assembly-side sensors 901 and 903 and the amount of rotation of the X-axis table support assembly side sensor 901 at a first time.

The one or more storage devices 1303 can be configured to store instructions that, when executed by the one or more processors 1301, cause the one or more processors 1301 to control the one or more storage devices 1303 to store the table support assembly-side data The one or more storage devices 1303 can be configured to store instructions that, when executed by the one or more processors 1301, cause the one or more processors 1301 to receive probe support assembly-side data indicative of the amount of rotation of the joint 505 about the axes parallel to the X-axis and the Y-axis at the first time.

The one or more storage devices 1303 can be configured to store instructions that, when executed by the one or more processors 1301, cause the one or more processors 1301 to control the one or more storage devices 1303 to store the probe support assembly-side data.

The one or more storage devices 1303 can be configured to store instructions that, when executed by the one or more processors 1301, cause the one or more processors 1301 to control the one or more storage devices 1303 to store imaging data acquired through the probe P at the first time in relation to the table support assembly-side data and the probe support assembly-side data acquired at the first time.

The one or more storage devices 1303 can be configured to store instructions that, when executed by the one or more processors 1301, cause the one or more processors 1301 to, at a second time subsequent to the first time, receive a first request from the user interface device 1307, and in response to the first request, retrieve the table support assembly-side data and the probe support assembly-side data from the one or more storage devices 1303, and display the retrieved table support assembly-side data and the probe support assembly-side data on the user interface device 1307.

The one or more storage devices 1303 can be configured to store instructions that, when executed by the one or more processors 1301, cause the one or more processors 1301 to, receive a second request from the user interface device 1307, and in response to the second request, control the one or more actuators of the actuator assembly 1100 to move the X-axis guide mechanism 301, the Y-axis guide mechanism 303 and the X-axis rotation mechanism 305 of the table support assembly 300 to thereby move and/or rotate the table 100 based on the table support assembly-side data, to reproduce the position and/or inclination of the table 100 detected at the first time.

The one or more storage devices 1303 can be configured to store instructions that, when executed by the one or more processors 1301, cause the one or more processors 1301 to, receive the second request from the user interface device 1307, and in response to the second request, control the one or more actuators of the actuator assembly 1100 to move one or more of the joints 505A-E of the probe support assembly 500 to thereby move and/or rotate the probe P gripped by the grip 501 based on the probe support assembly-side data, to reproduce the position and/or orientation of the probe P detected at the first time.

Reproduction of the position and/or inclination of the table 100 detected at the first time and reproduction of the position and/or orientation of the probe P detected at the first time through control of the actuator assembly 1100 by the one or more processors 1301 result in the elimination of operator error, increased accuracy and process efficiency, with the only variable being the operator's ability to reposition the subject on the table 100.

Figure 8:
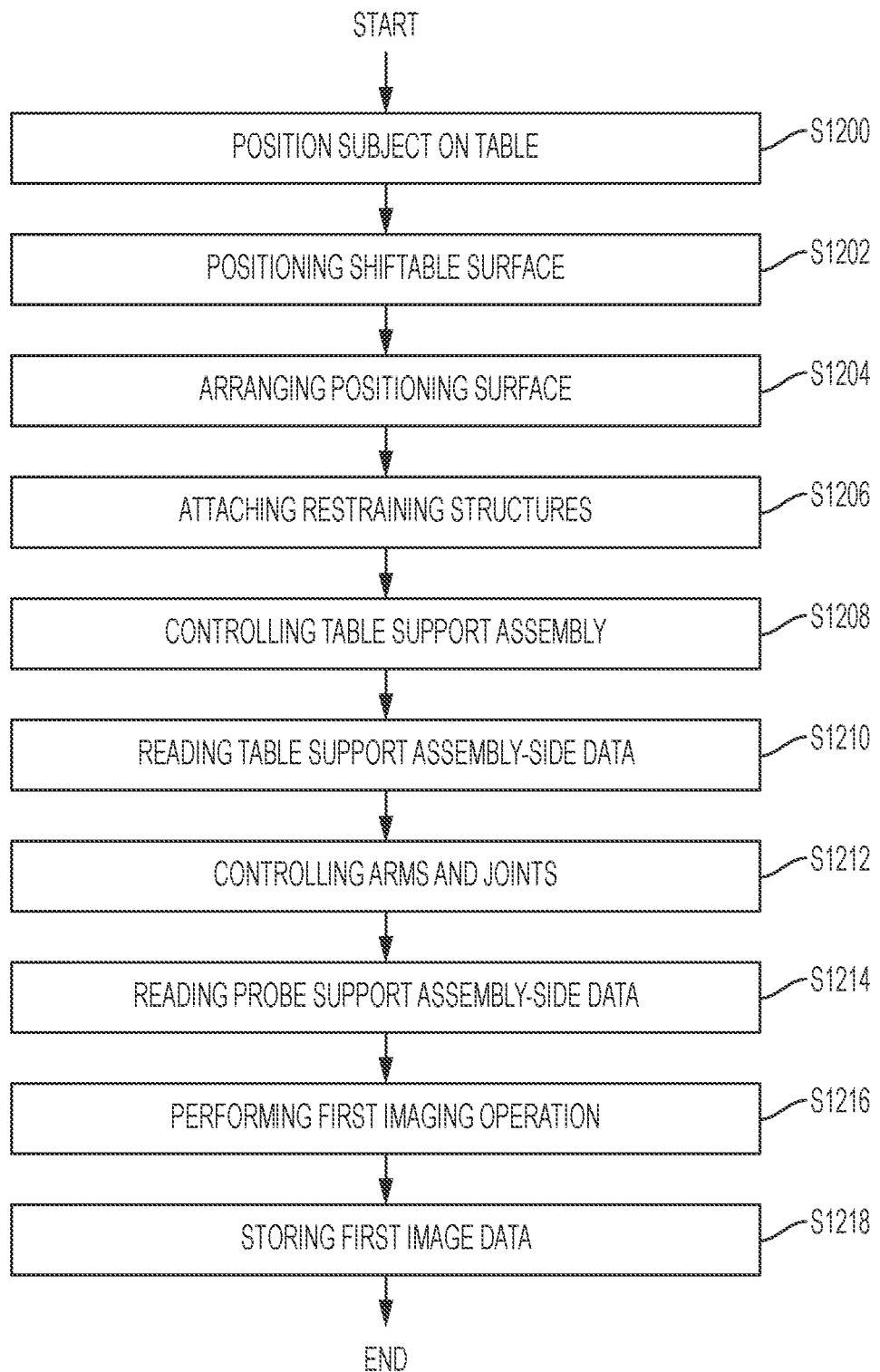
FIG. 8 shows a step of performing a first imaging routine as part of the method shown in FIG. 7.
Figure 9:
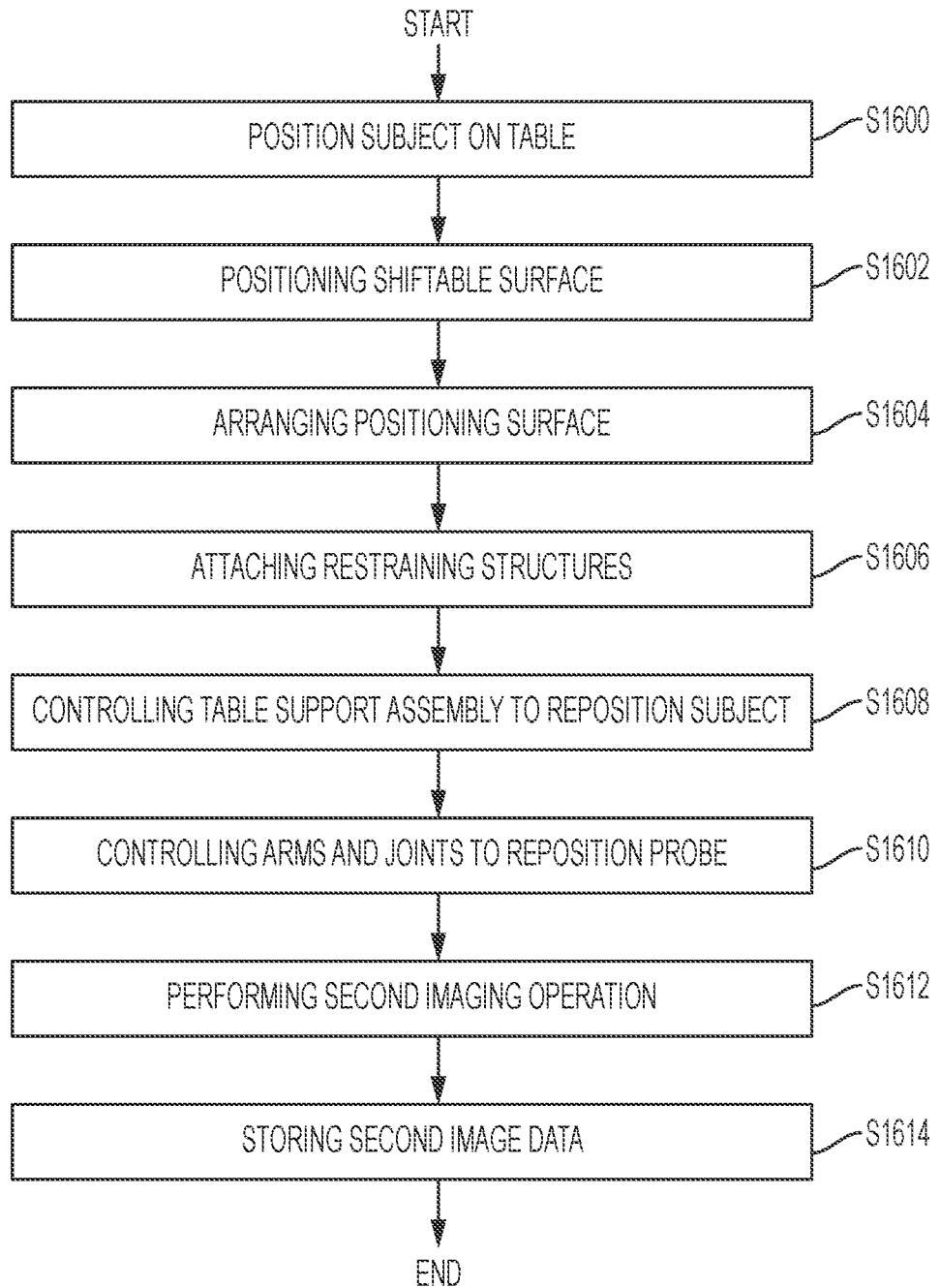
FIG. 9 shows a step of performing a second imaging routine as part of the method shown in FIG. 7.

A method according to another aspect of the invention is described below with reference to FIG. 7-9 of the drawings.

Figure 7:
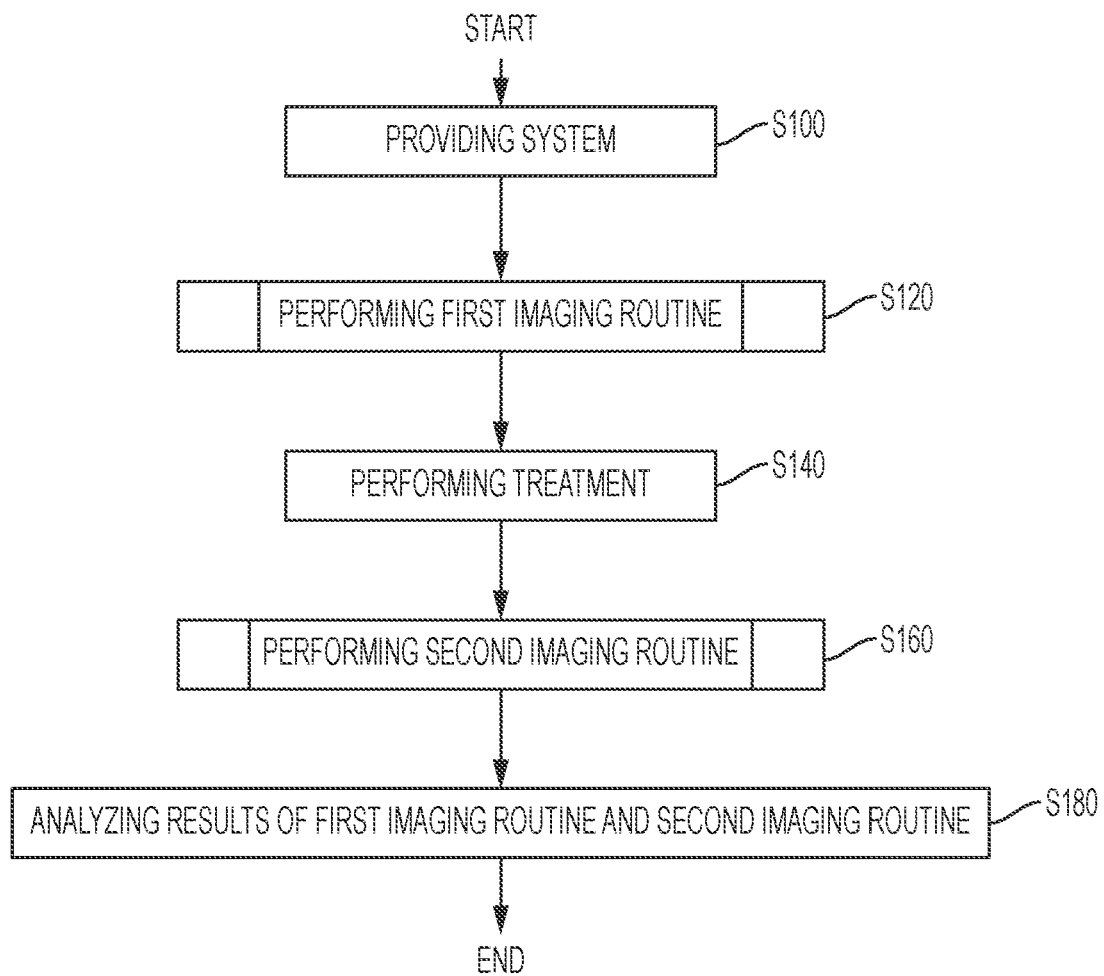
FIG. 7 shows a method according to another aspect of the invention.

As shown in FIG. 7, the method can include a step S100 of providing the system 10, a step S120 of performing a first imaging routine at the first time, a step S140 of performing a treatment on the subject S, a step S160 of performing a second imaging routine at the second time and a step S180 of analyzing results of the first imaging routine and the second imaging routine.

The step S120 of performing the first imaging routine will be described below with reference to FIG. 8 of the drawings.

The step S120 can include a step S1200 of positioning the subject S on the first cushion 107 and the second cushion 119 of the table 100 in an examination position.

The step S120 can include a step S1202 of positioning the shiftable surface 115 at one of the first position and the second position.

The step S120 can include a step S1204 of arranging the one or more positioning surfaces 123 and 125 on the first cushion 107 relative to the subject S to reduce the movement of the subject S in one or more directions parallel to the first cushion upper surface 109.

The step S120 can include a step S1206 of attaching the one or more retraining structures to the subject S and the first table frame 101 and the second table frame 117 to reduce the movement of the subject S.

The step S120 can include a step S1208 of manually controlling the table support assembly 300 or, controlling, through the controller 1300, the one or more actuators of the actuator assembly 1100 to move the X-axis guide mechanism 301, the Y-axis guide mechanism 303 and the X-axis rotation mechanism 305 of the table support assembly 300 to thereby move and/or rotate the table 100 in order to position the subject S.

The step S120 can include a step S1210 of reading the one or more table support assembly-side markers to determine the position of the table 100 relative to the arbitrary origin O and the degree of inclination of the table 100, and recording the position and inclination of the table 100. Further, the step 1210 can include causing the one or more processors 1301 to receive the table support assembly-side data output by and indicative of the positions of the one or more of table support assembly-side sensors 901 and 903 and the amount of rotation of the X-axis table support assembly side sensor 901 at the first time, and to record the table support assembly-side data.

The step S120 can include a step S1212 of manually controlling the arms 503A-D and the joints 505A-E to move the probe P held by the grip 501 to thereby position the probe P relative to the subject S. The probe P can be positioned at, for example, a position to capture one or more images of an internal organ of the subject S. More specifically, the probe P can be positioned at, for example, a position to capture one or more images of a section of a heart wall of heart of the subject S, where the one or more images can be later processed to determine a pre-treatment thickness of the section of the heart wall.

The step S120 can include a step S1214 of reading the one or more probe assembly-side markers to determine the amount of rotation of the joints 505A-E, and recording the amount of rotation of the joints 505A-E. Further, the step S1210 can include causing the one or more processors 1301 to receive the probe support assembly-side data output by the one or more of the X-axis probe support assembly-side sensor 905 and the Y-axis probe support assembly-side sensor, and to record the probe support assembly-side data.

The step S120 can include a step S1216 of performing a first imaging operation through the probe P to acquire first image data of at least a first image of the subject S.

The step S120 can include a step S1218 of causing the one or more processors 1301 to control the one or more storage devices 1303 to store the first image data acquired at the first time in relation to the table support assembly-side data and the probe support assembly-side data acquired at the first time.

The step S140 can include a step of performing a treatment on the subject S. As an example, the treatment can include a cardiovascular treatment to affect change in the thickness of the section of the heart wall of the subject S.

The step S160 can be performed after the step S140 to determine the efficacy of the treatment performed in the step S140.

The step S160 can include a step S1600 of positioning the subject S on the first cushion 107 and the second cushion 119 of the table 100 in the examination position of the first imaging routine.

The step S160 can include a step S1602 of positioning the shiftable surface 115 one of the first position and the second position in the same position as in the first imaging routine.

The step S160 can include a step S1604 of arranging the one or more positioning surfaces 123 and 125 on the first cushion 107 relative to the subject S to reduce the movement of the subject S in the one or more directions parallel to the first cushion upper surface 109.

The step S160 can include a step S1606 of attaching the one or more retraining structures to the subject S and the first table frame 101 and the second table frame 117 to reduce the movement of the subject S.

The step S160 can include a step S1608 of manually controlling the table support assembly 300 or, controlling, through the controller 1300, the one or more actuators of the actuator assembly 1100 to move the X-axis guide mechanism 301, the Y-axis guide mechanism 303 and the X-axis rotation mechanism 305 of the table support assembly 300 according to the table support assembly-side data read out from the one or more storage devices 1303 to thereby move and/or rotate the table 100 in order to position the subject S in the same position as in the first imaging routine.

The step S160 can include a step S1610 of manually controlling the arms 503A-D and the joints 505A-E according to the probe support assembly-side data read out from the one or more storage devices 1303 to move the probe P held by the grip 501 to thereby position and/or orient the probe P relative to the subject S in order to position the probe P in the same position and orientation as in the first imaging routine. The probe P can be positioned at, for example, the same position as in the first imaging routine to capture one or more images of the internal organ of the subject S. More specifically, the probe P can be positioned at, for example, the same position and orientation as in the first imaging routine to capture one or more images of the section of the heart wall of the subject S, where the one or more images can be later processed to determine a post-treatment thickness of the section of the heart wall.

The step S160 can include a step S1612 of performing a second imaging operation through the probe P to acquire second image data of at least a second image of the subject S.

The step S160 can include a step S1614 of causing the one or more processors 1301 to control the one or more storage devices 1303 to store the second image data acquired at the second time in relation to the table support assembly-side data and the probe support assembly-side data acquired at the second time.

The step S180 can include a step of causing the one or more processors 1301 to process the first image data to determine a value of a feature of the subject S prior to the treatment. As an example, the one or more processors 1301 can determine a pre-treatment thickness of a section of a heart wall of the subject S. The step S180 can include a step of causing the one or more processors 1301 to process the second image data to determine a value of the features of the subject S after the treatment. As an example, the one or more processors 1301 can determine a post-treatment thickness of the section of the heart wall of the subject S. The step S180 can include a step of causing the one or more processors 1301 to determine a difference between the post-treatment thickness and the pre-treatment thickness, and to determine whether the difference is equal to or greater than a predetermined value. An efficacy of the treatment can be decided based on the result of the determination of whether the difference is equal to or greater than the predetermined value.

By utilizing the system 10, the position and orientation of the subject S and the position and orientation of the probe P in the first imaging routine can be reproduced in the second imaging routine to allow for a more accurate comparison of the first image and the second image that reflects the efficacy of the treatment and minimizes the effects and/or noise caused by shifts in the positions and orientations of the subject S and the probe P in between the first imaging routine and the second imaging routine.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A system comprises:
a table assembly configured to support a subject in one or more examination positions;
a table support assembly configured to support the table assembly, wherein the table support assembly comprises:
one or more moving mechanisms configured to be controlled to move the table assembly relative to a reference point along one or more axes, and to rotate the table assembly around the one or more axes;
a probe support assembly comprising:
a grip configured to hold a probe of an ultrasound imaging device; and
an arrangement of a plurality of arms and joints configured to movably support the probe that is held by the grip, wherein the plurality of arms and joints provide multiple degrees of freedom,
wherein the probe support assembly is removably arranged at a predetermined position and orientation relative to the table support assembly to permit movement of the one or more moving mechanisms of the table support assembly and the plurality of arms and joints of the probe support assembly for reproduction of a position and orientation of the probe relative to the subject supported by the table assembly,
a sensor assembly comprising:
one or more table support assembly-side sensors configured to:
detect one or more of positions and inclinations of the table assembly; and
output position and inclination data indicative of the one or more positions and inclinations of the table assembly detected; and
one or more probe support assembly-side sensors configured to:
detect one or more of positions and inclinations of the probe; and
output position and inclination data indicative of the one or more positions and orientations of the probe detected.

2. The system according to claim 1,
wherein the table assembly comprises:
a first table frame comprising a first table frame upper surface and a first table frame lower surface; and
a first cushion supported by the first table frame upper surface of the first table frame, wherein the first cushion comprises a first cushion upper surface for supporting the subject in the one or more examination positions.

3. The system according to claim 2,
wherein the table assembly comprises:
a second table frame arranged on a side of the first table frame;
a second cushion supported by the second table frame, wherein the second cushion comprises a second cushion upper surface for supporting one or more legs of the subject in the one or more examination positions; and
an adjustable connector configured to connect the first table frame and the second table frame, wherein the adjustable connector is configured to be controlled to change a distance between the first table frame and the second table frame to accommodate a length of the one or more legs of the subject, and to be controlled to change an inclination between the first cushion upper surface and the second cushion upper surface.

4. The system according to claim 2,
wherein the table assembly comprises:
a shiftable surface configured to be controlled to shift from a first position to a second position,
wherein one or more sides of the first table frame and one or more sides of the first cushion define an access space through which to access the subject in a lateral recumbant position from a side of the first table frame lower surface,
wherein in the first position, the shiftable surface is arranged in the access space to support the subject, and
wherein in the second position, the shiftable surface is arranged away from the access space to permit access to the subject from the side of the first table frame lower surface.

5. The system according to claim 2,
wherein the table assembly comprises:
one or more positioning surfaces configured to be removably arranged on the first cushion upper surface relative to the subject to reduce movement of the subject in one or more directions parallel to the first cushion upper surface,
wherein the one or more positioning surfaces comprises a pair of positioning surfaces, wherein the pair of positioning surfaces are spaced apart to accommodate a tail of the subject, the subject being supported by the first cushion upper surface in a supine position or a semi-Fowler's position to reduce movement of the subject in a direction of gravity upon tilting of the first table frame.

6. The system according to claim 2,
wherein the table assembly comprises:
one or more restraining devices configured to be removably attached to the first table frame, wherein the one or more restraining devices are configured to reduce movement of the subject supported by the first cushion.

7. The system according to claim 1,
wherein the one or more moving mechanisms comprises one or more guides to guide one or more translational movements of the table assembly along the one or more axes, and one or more rotational movements around the one or more axes.

8. The system according to claim 1,
wherein the table support assembly comprises:
one or more table support assembly-side markers indicative of a position of the table assembly along the one or more axes, and a degree of inclination around the one or more axes.

9. The system according to claim 1,
wherein the probe support assembly comprises:
one or more probe support assembly-side markers indicative of positions and orientations of the probe held by the grip.

10. The system according to claim 1, further comprising:
an actuator assembly comprising:
one or more table support assembly-side actuators configured to move the one or more moving mechanisms of the table support assembly to move the table assembly along the one or more axes, and to rotate the table assembly around the one or more axes; and
one or more probe support assembly-side actuators configured to move the plurality of arms and joints to change a position and orientation of the probe.

11. The system according to claim 10, further comprising:
a controller comprising:
one or more processors; and
one or more storage devices configured to store instructions that, when executed by the one or more processors, cause the one or more processors to:
receive the position and inclination data indicative of the one or more positions and inclinations of the table assembly detected by the one or more table support assembly-side sensors at a first time;
control the one or more storage devices to store the position and inclination data indicative of the one or more positions and inclinations of the table assembly detected;
receive the position and inclination data indicative of the one or more positions and orientations of the probe detected by the one or more probe support assembly-side sensors at the first time; and
control the one or more storage devices to store the one or more positions and orientations of the probe detected.

12. The system according to claim 11,
wherein the instructions, when executed by the one or more processors, cause the one or more processors to:
control the one or more storage devices to store imaging data acquired through the probe of the ultrasound imaging device in relation to the position and inclination data indicative of the one or more positions and inclinations of the table assembly detected at the first time, and in relation to the one or more positions and orientations of the probe detected at the first time.

13. The system according to claim 12,
wherein the instructions, when executed by the one or more processors, cause the one or more processors to:
in response to a request, retrieve from the one or more storage devices and control a display to display:
the position and inclination data indicative of the one or more positions and inclinations of the table assembly detected at the first time; and
the one or more positions and orientations of the probe detected at the first time.

14. The system according to claim 12,
wherein the instructions, when executed by the one or more processors, cause the one or more processors to:
in response to a request,
control the one or more table support assembly-side actuators based on the position and inclination data indicative of the one or more positions and inclinations of the table assembly detected at the first time, to reproduce the one or more positions and inclinations of the table assembly detected at the first time; and
control the one or more probe support assembly-side actuators based on the one or more positions and orientations of the probe detected at the first time, to reproduce the one or more positions and orientations of the probe detected at the first time.

15. A method comprising:
performing a first process comprising:
positioning a subject to be supported by a table assembly in an examination position;
controlling one or more moving mechanisms of a table support assembly supporting the table assembly to move the table assembly relative to a reference point along one or more axes, and to rotate the table assembly around the one or more axes;
detecting, through one or more table support assembly-side sensors of a sensor assembly, one or more of positions and inclinations of the table assembly;
outputting position and inclination data indicative of the one or more positions and inclinations of the table assembly detected;
operating a grip of a probe support assembly to hold a probe of an ultrasound imaging device;
controlling an arrangement of a plurality of arms and joints of the probe support assembly, wherein the plurality of arms and joints provide multiple degrees of freedom, to movably support the probe that is held by the grip;
detecting, through one or more probe support assembly-side sensors of the sensor assembly, one or more positions and inclinations of the probe; and
output position and inclination data indicative of the one or more positions and orientations of the probe detected; and
performing a second process comprising:
positioning the subject to be supported by the table assembly in the examination position; and
controlling the one or more moving mechanisms of the table support assembly based on the position and inclination data indicative of the one or more positions and inclinations of the table assembly detected, to move the table assembly relative to the reference point along the one or more axes, and to rotate the table assembly around the one or more axes, and controlling the arrangement of the plurality of arms and joints of the probe support assembly based on the position and inclination data indicative of the one or more positions and orientations of the probe detected, to reproduce a position and orientation of the probe relative to the subject supported by the table assembly.

16. The method according to claim 15, wherein the first process further comprises performing a first imaging operation using the probe, wherein the method further comprises performing, between performing the first process and performing the second process, a cardiovascular treatment on the subject and wherein the second process further comprises performing a second imaging operation using the probe.

* * * * *